US006479641B2

(12) United States Patent
Whelihan

(10) Patent No.: US 6,479,641 B2
(45) Date of Patent: Nov. 12, 2002

(54) BINDING MOIETIES FOR HUMAN PARVOVIRUS B19

(75) Inventor: E. Fayelle Whelihan, South Boston, MA (US)

(73) Assignee: Dyax Corp., Cambridge, MA (US)

( * ) Notice: Subject to any disclaimer, the term of this patent is extended or adjusted under 35 U.S.C. 154(b) by 0 days.

(21) Appl. No.: 09/881,276

(22) Filed: Jun. 14, 2001

(65) Prior Publication Data

US 2002/0031761 A1 Mar. 14, 2002

Related U.S. Application Data

(62) Division of application No. 09/669,271, filed on Sep. 26, 2000, now Pat. No. 6,291,197, which is a division of application No. 09/186,958, filed on Nov. 5, 1998, now Pat. No. 6,238,860.

(51) Int. Cl.[7] .................................................. C07K 16/00

(52) U.S. Cl. ................................ 530/388.3; 530/387.1; 530/327; 424/147.1

(58) Field of Search ............................ 435/5, 7.5, 7.92; 530/387.1, 388.3, 327; 424/147.1

(56) References Cited

U.S. PATENT DOCUMENTS

| | | | |
|---|---|---|---|
| 5,223,409 A | | 6/1993 | Ladner et al. |
| 5,436,127 A | | 7/1995 | Yahata et al. |
| 5,449,608 A | | 9/1995 | Young et al. |
| 5,498,413 A | | 3/1996 | Alvarez et al. |
| 5,508,186 A | | 4/1996 | Young et al. |
| 5,585,254 A | | 12/1996 | Maxwell et al. |
| 5,785,974 A | | 7/1998 | Alvarez et al. |
| 5,916,563 A | | 6/1999 | Young et al. |
| 6,001,371 A | | 12/1999 | Young et al. |
| 6,274,307 B1 | * | 8/2001 | Sout Schek et al. ............ 435/5 |

FOREIGN PATENT DOCUMENTS

| | | | |
|---|---|---|---|
| EP | 0 554 414 B1 | 8/1993 | .......... A61K/39/23 |
| EP | 0 647 655 A1 | 4/1995 | ............ C07K/7/10 |
| WO | WO 90/13567 | 11/1990 | .......... A61K/39/23 |
| WO | WO 91/04330 | 4/1991 | ........... C12N/15/35 |
| WO | WO 91/12269 | 9/1991 | ........... C07K/13/00 |
| WO | WO 94/17098 | 8/1994 | ............ C07K/7/10 |
| WO | WO 97/46251 | 12/1997 | .......... A61K/38/03 |

OTHER PUBLICATIONS

Anderson et al., *Virology*, 206:626–632 (1995).
Arakelov et al., *J. Infectious Disease*, 168:580–585 (1993).
Bansal et al., *J. Infectious Disease*, 167:1034–1044 (1993).
Brown et al., *J. Virological Meth.*, 29:53–62 (1990).
Brown et al., *Virus Res.*, 15:197–212 (1990).
Brown et al., *J. Virology*, 65: 2702–2706 (1991).
Brown et al., *J. Virology*, 66: 6989–6996 (1992).
Brown et al., *Science*, 262:114–117 (1993).
Cosart et al., *Lancet*, I: 72–73 (1975).
Fridell et al., *J. Clin. Microbiol.*, 29:1376–1381 (1991).
Gray et al., *J. Virological Meth.*, 44:11–24 (1993).
Kajigaya et al., *PNAS USA*, 88:4646–4650 (1991).
Kovacs et al., *Am. J. Obstet. Gynecol.*, 167: 461–466 (1992).
Kurtzman et al., *N. Engl. J. Med.*, 321:519–523 (1989).
Kurtzman et al., *J. Clin Invest.*, 84:1114–1123 (1989).
Loughrey et al., *J. Med. Virol.*, 39:97–100 (1993).
Merrifield, *J. Am. Chem. Soc.*, 85:2149–2154 (1963).
Morey et al., *J. Clin. Pathol.*, 45:673–678 (1992).
Morey et al., *Histochemical J.*, 25: 421–429 (1993).
Musiani et al., *J. Med. Virol.*, 40: 157–160 (1993).
O'Neil et al., *Arch. Virol.*, 123:125–134 (1992).
Ozawa et al., *Science*, 233:883–886 (1986).
Rayment et al., *J. Gen. Virol.*, 71:2665–2672 (1990).
Rosenfeld et al., *J. Clin. Invest.*, 89:2023–2029 (1992).
Rosenfeld et al., *Arch Virol.*, 136:9–18 (1994).
Saikawa et al., *J. Virol*, 67:3004–3009 (1993).
Salimans et al., *J. Virol. Meth*, 39:247–258 (1992).
Sato et al., *J. Virol.*, 65:1667–1672 (1991).
Sato et al., *J. Virol.*, 65:5485–5490 (1991).
Schwarz et al., *Scan. J. Infect. Dis.*, 24:691–696 (1992).
Schwarz et al., *J. Virol.*, 66:1273–1276 (1992).
Shade et al., *J. Virol.*, 58:921–936 (1986).
Sosa et al., *J. Med. Virol.*, 36:125–130 (1992).
Torok et al., *Clin. Infect. Dis.*, 14:149–155 (1992).
Yaegashi et al., *J. Virol.*, 63:2422–2426 (1989).

* cited by examiner

*Primary Examiner*—Laurie Scheiner
(74) *Attorney, Agent, or Firm*—Leon R. Yankwich

(57) ABSTRACT

Methods for detecting human parvovirus B19 in and removing it from biological samples such as blood are disclosed, together with reagents suitable for the purpose comprising binding moieties that recognize human parvovirus B19 and/or B19-like polypeptide and form a binding complex therewith. Preferred polypeptide binding moieties are particularly disclosed.

1 Claim, 1 Drawing Sheet

SEQUENCE LISTING

```
<160> NUMBER OF SEQ ID NOS: 27

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide
<221> NAME/KEY: variant
<222> LOCATION: (1)..(11)
<223> OTHER INFORMATION: amino acid positions designated Xaa may be
      varied to form alternative parvovirus B19 binders, as
      explained in the disclosure; Cys residues are invariant

<400> SEQUENCE: 1

Xaa Xaa Cys Xaa Xaa Xaa Xaa Xaa Cys Xaa Xaa
1               5                   10


<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: parvovirus
      B19 binding polypeptide
<221> NAME/KEY: variant
<222> LOCATION: (1)..(12)
<223> OTHER INFORMATION: amino acid positions designated Xaa may be
      varied to form alternative parvovirus B19 binders, as
      explained in the disclosure; specified Phe, Trp and
      Cys residues are invariant

<400> SEQUENCE: 2

Xaa Phe Cys Xaa Xaa Trp Xaa Xaa Xaa Cys Xaa Xaa
1               5                   10


<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide
<221> NAME/KEY: variant
<222> LOCATION: (1)..(11)
<223> OTHER INFORMATION: amino acid positions designated Xaa may be
      varied to form alternative parvovirus B19 binders, as
      explained in the disclosure; Cys residues are invariant

<400> SEQUENCE: 3

Xaa Cys Xaa Xaa Xaa Xaa Xaa Xaa Xaa Cys Xaa
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: parvovirus
```

-continued

```
      B19 binding polypeptide

<400> SEQUENCE: 4

Phe Phe Cys Gly Phe Trp His Asp Cys His Pro
1               5                   10


<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide

<400> SEQUENCE: 5

Phe Ser Cys Leu Trp Phe Pro Phe Cys Pro Asp
1               5                   10


<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide

<400> SEQUENCE: 6

Phe Phe Cys Ala Leu Trp Pro Ser Cys His His
1               5                   10


<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide

<400> SEQUENCE: 7

Leu Phe Cys His Phe Trp Tyr Asn Cys Asp Phe
1               5                   10


<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide

<400> SEQUENCE: 8

Leu Phe Cys Ser Phe Trp Tyr Asn Cys Asp Ala
1               5                   10


<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: parvovirus
      B19 binding polypeptide

<400> SEQUENCE: 9

Leu Phe Cys Ser Phe Trp Tyr Asn Cys Asp Asp
1               5                   10


<210> SEQ ID NO 10
```

-continued

<211> LENGTH: 11
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 10

Leu Phe Cys Arg Phe Trp Tyr Asn Cys Ser Ala
1 5 10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 11

Phe Phe Cys Gln Tyr Trp Tyr Asn Cys Asp
1 5 10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 12

Phe Cys Arg Phe Trp Tyr Gly Cys His Pro
1 5 10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 13

Phe Phe Cys Ser Phe Trp His Gly Gly Cys Asp Asp
1 5 10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 14

Ala Phe Cys His Phe Trp Phe His Gly Cys Asp Asp
1 5 10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 15

-continued

Ala Phe Cys Trp Lys Trp Pro Gly Asn Cys Lys His
1 5 10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 16

His Phe Cys His Phe Trp Phe Gly Gly Cys Pro His
1 5 10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 17

Phe Cys Trp Leu Trp Pro Ser Ser Asp Cys Phe
1 5 10

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 18

Phe Cys Trp Leu Trp Pro Ala His Ser Cys His
1 5 10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 19

Phe Cys His Leu Trp Trp Pro Phe Gln Cys Ala
1 5 10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 20

Phe Cys Gln Leu Trp Trp Pro Phe Gln Cys Ala
1 5 10

<210> SEQ ID NO 21
<211> LENGTH: 11
<212> TYPE: PRT
<213> ORGANISM: Artificial Sequence
<220> FEATURE:

-continued

<223> OTHER INFORMATION: Description of Artificial Sequence: parvovirus B19 binding polypeptide

<400> SEQUENCE: 21

```
Leu Cys Pro Ala His Trp Gln Phe Trp Cys Asp
1               5                   10
```

<210> SEQ ID NO 22
<211> LENGTH: 26
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 22

```
Ala Glu Gly Thr Gly Asp Phe Cys Ser Phe Trp His Gly Gly Cys Asp
1               5                   10                  15

Asp Asp Pro Gly Pro Glu Gly Gly Gly Ser
            20                  25
```

<210> SEQ ID NO 23
<211> LENGTH: 26
<212> TYPE: PRT
<213> ORGANISM: Artificial Sequence
<220> FEATURE:
<223> OTHER INFORMATION: Description of Artificial Sequence: parvovirus B19 binding polypeptide

<400> SEQUENCE: 23

```
Ala Glu Gly Thr Gly Asp Phe Cys Trp Leu Trp Pro Ala His Ser Cys
1               5                   10                  15

His Asp Pro Gly Pro Glu Gly Gly Gly Ser
            20                  25
```

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: microprotein template
<221> NAME/KEY: variant
<222> LOCATION: (1)..(11)
<223> OTHER INFORMATION: amino acid positions designated Xaa are variegated to build a library of binding loop analogues, as explained in the disclosure; Cys residues are invariant

<400> SEQUENCE: 24

```
Xaa Xaa Cys Xaa Xaa Xaa Xaa Xaa Cys Xaa Xaa
1               5                   10
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: microprotein template
<221> NAME/KEY: variant
<222> LOCATION: (1)..(12)
<223> OTHER INFORMATION: amino acid positions designated Xaa are variegated to build a library of binding loop analogues, as explained in the disclosure; Cys residues are invariant

<400> SEQUENCE: 25

```
Xaa Xaa Cys Xaa Xaa Xaa Xaa Xaa Cys Xaa Xaa Xaa
1               5                   10
```

-continued

```
<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence:
      microprotein template
<221> NAME/KEY: variant
<222> LOCATION: (1)..(11)
<223> OTHER INFORMATION: amino acid positions designated Xaa are
      variegated to build a library of binding loop analogues, as
      explained in the disclosure; Cys residues are invariant

<400> SEQUENCE: 26

Xaa Xaa Cys Xaa Xaa Xaa Xaa Xaa Cys Xaa Xaa
1               5                   10


<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence:
      N-terminal linker sequence

<400> SEQUENCE: 27

Glu Gly Gly Gly Ser
1               5
```

BINDING MOIETIES FOR HUMAN PARVOVIRUS B19

CROSS-REFERENCE TO RELATED APPLICATIONS

This application is a division of U.S. application Ser. No. 09/669,271, filed Sep. 26, 2000, now U.S. Pat. No. 6,291,197 B1, which is a division of U.S. application Ser. No. 09/186,958, filed Nov. 5, 1998, now U.S. Pat. No. 6,238,860, the entirety of which is hereby incorporated by reference.

FIELD OF THE INVENTION

The present invention relates to methods and materials for detecting, clearing, or isolating parvovirus B19 and/or B19-like polypeptides from blood or other solutions containing it. The invention particularly provides polypeptides and recombinant bacteriophage expressing such polypeptides that are capable of binding to parvovirus B19 and/or B19-like polypeptides for the purpose of detecting, clearing, or isolating parvovirus B19 and/or B19-like viruses or polypeptides.

BACKGROUND OF THE INVENTION

Parvoviruses form the parvoviridea family which are common agents of animal diseases. Parvovirus B19 is thus far the only strain identified to infect humans. The first strong link between parvovirus B19 infection and human disease was reported by Cossart et al. in England during screening of healthy blood donors for hepatitis B surface antigen. See, Cossart et al., *Lancet,* I: 72–73 (1975). "B19" refers to the designation of the sample from which this parvovirus was first isolated, and as the strain that is capable of infecting humans, it is often referred to as "human parvovirus B19".

Parvovirus B19 is a non-enveloped, single-stranded DNA virus with a diameter of 22 nm, consisting of only the genome and a few structural and non-structural proteins. The capsid proteins are arranged with icosahedral symmetry and enclose the genome of approximately 5500 base pairs. Two large open reading frames are in the viral genome: The left open reading frame codes for non-structural proteins (NS1 and NS2) involved in viral replication and packaging; the right open reading frame codes for the structural proteins forming the viral capsid, VP1(781 amino acids) and VP2 (554 amino acids). Both structural proteins are in the same reading frame and the entire sequence of VP2 is contained within VP1. VP2 is the major protein of the B19 capsid.

Parvovirus B19 is among the most resistant viruses known and has been identified as the causative agent of several diseases, including transient aplastic crisis (TAC) of hemolytic disease, the common childhood rash called "fifth disease", a polyarthralgia syndrome in normal adults that may be chronic and that resembles rheumatoid arthritis in its clinical features, and some forms of chronic anemia and/or neutrpenia. Pregnant women infected with this virus frequently suffer serious disabilities including spontaneous abortion and hydrops fetalis.

As a blood-borne virus, parvovirus B19 has become a concern for organizations dealing with whole blood or blood products intended, e.g., for use in transfusions. Therefore, it is important to develop sensitive methods for detection of the virus in infected blood and methods for clearing the virus from blood drawn from an infected subject.

Techniques employing Polymerase Chain Reaction (PCR) have become prevalent in recent years for detecting the presence of parvovirus B19 in biological samples. For example, Schwarz et al. utilized a pair of oligonucleotide primers spanning the PstI-fragment of the B19 virus genome to detect the B19 viral DNA in sera of individuals in the incubation period and acute phase of parvovirus B19 infection. See, Schwarz et al., *Scand. J Infect. Dis.,* 24:691–696 (1992). See, also, Musiani et al., who utilized nested PCR to detect B19 infection in immunocompromised patients (*J. Med. Virol.,* 40:157–160 (1993)), and also Torok et al., who employed PCR as a tool to diagnose prenatal intrauterine infection with parvovirus B19 (*Clin. Infect. Dis.,* 14:149–155 (1992)).

Another approach taken to detect the presence of viral products in the infected individual is the use of in situ hybridization with detectable probes. For example, Morey et al. reported intracellular localization of parvovirus B19 nucleic acid by in situ hybridization with digoxiginin-labeled probes (*Histochemical Journal,* 25:421–429 (1993)). Later the same group employed a non-isotopic in situ hybridization technique in identifying parvovirus B19 infected cells using biotinylated probes (*J. Clin. Pathol.,* 45: 673–678 (1992)). Although in situ hybridization is a rapid and specific means for localizing viral nucleic acid with a high degree of resolution, the sensitivity of this system is limited by the fact that hybridization occurs only at the surface of the section.

Further development of such assays has been hampered because parvovirus B19 cannot be isolated in conventional cell cultures and has only been propagated successfully in cultures of human bone marrow (Ozawa et al., *Science,* 233:883–886, (1986)), umbilical cord blood (Sosa et al., *J Med. Virol.,* 36:125–130, (1992)), fetal liver (Yaegashi et al., *J. Virol.,* 63:6,2422–2426, (1989)), and cultures from peripheral blood stimulated by erythropoietin (Schwarz et al., *J. Virol.,* 66:1273–1276, (1992)). Another obstacle for development of such assays has been the possible existence of other parvoviruses and isotypes of parvovirus B19 that may also infect humans.

There is still a need, therefore, for sensitive and effective assays to detect the presence of B19 and/or B19-like viruses and subcomponents thereof, for ways to clear B19 and/or B19-like polypeptides from samples containing it (them), and for reagents that can bind B19 and/or B19-like polypeptides and which will be useful for detecting the presence of and/or clearing such viruses or polypeptides from samples, including blood.

In answer to the foregoing needs, a group of non-naturally occurring polypeptides has now been surprisingly discovered that bind specifically to parvovirus B19 and related polypeptides. Utilizing phage display technology, recombinant bacteriophage displaying polypeptides that recognize and bind to B19 capsid proteins have been identified and isolated. The phage products and isolated polypeptides have proved to be valuable reagents for effective detection and isolation of the B19 virus and B19-like polypeptides.

SUMMARY OF THE INVENTION

The present invention provides binding moieties for parvovirus B19 and/or B19-like viruses and polypeptide subcomponents of such viruses. Preferred binding moieties described herein are polypeptides and recombinant bacteriophage displaying such peptides which bind to parvovirus B19 and/or B19-like viruses, and most preferably to the virus's capsid proteins VP1 and/or VP2.

In specific embodiments, the invention provides binding moieties for B19 and/or B19-like polypeptides as well as methods for detection and removal of human parvovirus B19 and/or B19-like polypeptides from samples (particularly human whole blood or blood products) containing it. In particular, preferred embodiments disclosed herein provide polypeptides that bind to parvovirus B19 capsid proteins VP1 or VP2 or combinations of such proteins and provide methods for binding and/or removing such capsid proteins from solutions containing them. Preferred features include recombinant bacteriophage expressing exogenous DNA encoding parvovirus B19 binding polypeptides.

A preferred binding moiety for human parvovirus B19 and/or B19-like polypeptides according to this invention will be a polypeptide having an amino acid sequence including a sequence selected from the group consisting of:

I. $X_1$-$X_2$-Cys-$X_3$-$X_4$-$X_5$-$X_6$-$X_7$-Cys-$X_8$-$X_9$ (SEQ ID NO:1), wherein $X_1$ is Phe or Leu or is not present; $X_2$ is Phe or Ser; $X_3$ is Arg, Gln, Ser, His, Ala, Leu, or Gly; $X_4$ is Phe, Tyr, Leu, or Trp; $X_5$ is Trp or Phe; $X_6$ is Tyr, Pro, or His; $X_7$ is Gly, Asn, Ser, Phe, or Asp; $X_8$ is His, Asp, Ser or Pro; $X_9$ is Pro, Ala, Phe, His, or Asp or is not present;

II. $X_{10}$-Phe-Cys-$X_{11}$-$X_{12}$-Trp-$X_{13}$-$X_{14}$-$X_{15}$-Cys-$X_{16}$-$X_{17}$ (SEQ ID NO:2), wherein $X_{10}$ is His, Ala, or Phe; $X_{11}$ is His, Trp, or Ser; $X_{12}$ is Phe or Leu; $X_{13}$ is Phe, Pro, or His; $X_{14}$ is Gly or His; $X_{15}$ is Gly or Asn; $X_{16}$ Pro, Leu, or Asp; $X_{17}$ is His or Asp; and III. $X_{18}$-Cys-$X_{19}$-$X_{20}$-$X_{21}$-$X_{22}$-$X_{23}$-$X_{24}$-$C_{25}$-Cys-$X_{26}$ (SEQ ID NO:3), wherein $X_{18}$ is Phe or Leu; $X_{19}$ is Trp, His, Gln or Pro; $X_{20}$ is Leu or Ala; $X_{21}$ is Trp or His; $X_{22}$ is Pro or Trp; $X_{23}$ is Ser, Ala, Pro or Gln; $X_{24}$ is Ser, His, or Phe; $X_{25}$ is Asp, Ser, Gln or Trp; and $X_{26}$ is Phe, His, Ala or Asp.

Particularly preferred polypeptides of the invention include the following sequences:

Phe-Phe-Cys-Gly-Phe-Trp-His-Asp-Cys-His-Pro (SEQ ID NO:4);

Phe-Ser-Cys-Leu-Trp-Phe-Pro-Phe-Cys-Pro-Asp (SEQ ID NO:5);

Phe-Phe-Cys-Ala-Leu-Trp-Pro-Ser-Cys-His-His (SEQ ID NO:6);

Leu-Phe-Cys-His-Phe-Trp-Tyr-Asn-Cys-Asp-Phe (SEQ ID NO:7);

Leu-Phe-Cys-Ser-Phe-Trp-Tyr-Asn-Cys-Asp-Ala (SEQ ID NO:8);

Leu-Phe-Cys-Ser-Phe-Trp-Tyr-Asn-Cys-Asp-Asp (SEQ ID NO:9);

Leu-Phe-Cys-Arg-Phe-Trp-Tyr-Asn-Cys-Ser-Ala (SEQ ID NO:10);

Phe-Phe-Cys-Gln-Tyr-Trp-Tyr-Asn-Cys-Asp (SEQ ID NO:11);

Phe-Cys-Arg-Phe-Trp-Tyr-Gly-Cys-His-Pro (SEQ ID NO:12);

Phe-Phe-Cys-Ser-Phe-Trp-His-Gly-Gly-Cys-Asp-Asp (SEQ ID NO:13);

Ala-Phe-Cys-His-Phe-Trp-Phe-His-Gly-Cys-Asp-Asp (SEQ ID NO:14);

Ala-Phe-Cys-Trp-Lys-Trp-Pro-Gly-Asn-Cys-Lys-His (SEQ ID NO:15);

His-Phe-Cys-His-Phe-Trp-Phe-Gly-Gly-Cys-Pro-His (SEQ ID NO:16);

Phe-Cys-Trp-Leu-Trp-Pro-Ser-Ser-Asp-Cys-Phe (SEQ ID NO:17);

Phe-Cys-Trp-Leu-Trp-Pro-Ala-His-Ser-Cys-His (SEQ ID NO:18);

Phe-Cys-His-Leu-Trp-Trp-Pro-Phe-Gln-Cys-Ala (SEQ ID NO:19);

Phe-Cys-Gln-Leu-Trp-Trp-Pro-Phe-Gln-Cys-Ala (SEQ ID NO:20); and

Leu-Cys-Pro-Ala-His-Trp-Gln-Phe-Trp-Cys-Asp (SEQ ID NO:21).

Especially preferred embodiments include the polypeptides:

Ala-Glu-Gly-Thr-Gly-Asp-Phe-Phe-Cys-Ser-Phe-Trp-His-Gly-Gly-Cys-Asp-Asp-Asp-Pro-Gly-Pro-Glu-Gly-Gly-Gly-Ser (SEQ ID NO:22) and Ala-Glu-Gly-Thr-Gly-Asp-Phe-Cys-Trp-Leu-Trp-Pro-Ala-His-Ser-Cys-His-Asp-Pro-Gly-Pro-Glu-Gly-Gly-Gly-Ser (SEQ ID NO:23).

The present invention also provides binding moieties that are capable of binding human parvovirus B19 and/or B19-like viruses and dissociating from the virus under specific solution conditions. For example, preferred embodiments according to this invention bind to B19 at physiological pH and dissociate at low pH (e.g., pH 2).

Also included in the present invention are non-peptide and modified peptides that bind parvovirus B19 and/or parvovirus B19-like polypeptides. An example of these modifications is a constrained-loop peptide having paired cysteine residues that form disulfide bonds, modified at one cysteine residue by substitution of the cysteine with non-natural amino acid having a carboxylic acid side chain capable of condensing to form a stable thioester bridge. Such cyclic thioester analogues of synthetic peptides are described in PCT publication WO 97/46251, incorporated herein by reference. Other specifically contemplated modifications include N-terminal or C-terminal modifications of linkers such as poly-glycine segments and alterations to include functional groups, notably hydrazide (—NH—$NH_2$) functionalities, to assist in immobilization of binding peptides according to this invention on solid supports.

The present invention also provides a method of detecting human parvovirus B19 and/or B19-like viruses in a solution suspected of containing it comprising the steps of contacting the solution with a binding moiety according to the invention and detecting whether binding of the peptide to the virus has occurred. The present invention also provides a method of removing human parvovirus from a solution containing it comprising the steps of immobilizing a B19 binding moiety on a chromatographic support, and contacting a solution containing human parvovirus B19 with the chromatographic material.

The present invention also provides a recombinant bacteriophage, i.e., bacteriophage transfected with exogenous DNA, that express one or more human parvovirus B19 binding peptides. Finally, the present invention provides a method for detecting human parvovirus B19 and/or B19-like polypeptides in a sample such as blood suspected of containing the virus, comprising the steps of contacting the blood with a bacteriophage expressing exogenous DNA encoding a human parvovirus B19 binding peptide, and detecting if binding has occurred between the peptide displayed on the bacteriophage and virus.

Definitions

In the following sections, the term "recombinant" is used to describe non-naturally altered or manipulated nucleic acids, host cells infected with exogenous nucleic acids, or polypeptides expressed non-naturally, through manipulation of isolated DNA and transformation of host cells. Recombinant is a term that specifically encompasses DNA molecules which have been constructed in vitro using genetic engineering techniques, and use to the term "recombinant" as an adjective to describe a molecule, construct, vector, cell, polypeptide or polynucleotide specifically excludes naturally occurring such molecules, constructs, vectors, cells, polypeptides or polynucleotides.

As used herein, the term "B19-like polypeptide" refers to any subcomponent of parvovirus B19 or fragment of the whole B19 virus that is immunologically cross-reactive with parvovirus B19, including immunologically reactive fragments of the capsid and the tail. Capsid proteins VP1 and VP2, or combinations thereof, whether associated with the whole virus or isolated or synthetically prepared, are all specifically within the definition of the term "B19-like polypeptide". The term also refers to other whole viruses and their subcomponents immunologically cross-reactive with B19, including all parvovirus B19 isotypes and any fragments of the isotypes, including but not limited to the isotypes that lead to clinical symptoms in humans.

The term "bacteriophage" is defined as a bacterial virus containing a DNA core and a protective shell built up by the aggregation of a number of different protein molecules.

The terms "bacteriophage" and "phage" are used herein interchangeably.

The term "binding moiety" as used herein refers to any molecule, polypeptide, peptidomimetic or transformed cell ("transformant") capable of forming a binding complex with another molecule, polypeptide, peptidomimetic or tranformant. A "B19 binding moiety" is a binding moiety that forms a complex with parvovirus B19 or B19-like polypeptides. Specific examples of B19 binding moieties are the polypeptides mentioned above (SEQ ID NOs:1–23) and bacteriophage displaying any of such polypeptides. Also included within the definition of B19 binding moieties are polypeptides derived from a polypeptide having an amino acid sequence according to formula I, II or III, above, which have been modified for particular results (in addition to B19 or like polypeptide binding ability). Specific examples of modifications contemplated are COOH—or N-terminal amino acid substitutions or polypeptide chain elongations for the purpose of linking the binding moiety to a chromatographic support or other substrate, and substitutions of one or more cysteine residues that normally form disulfide links, for example with non-naturally occurring amino acid residues having reactive side chains, for the purpose of forming a more stable bond between those amino acid positions than the former disulfide bond. All such modified B19 binding moieties are also considered B19 binding moieties so long as they retain the ability to bind parvovirus B19 or B19-like polypeptides.

DETAILED DESCRIPTION OF THE PREFERRED EMBODIMENTS

Figure 1:
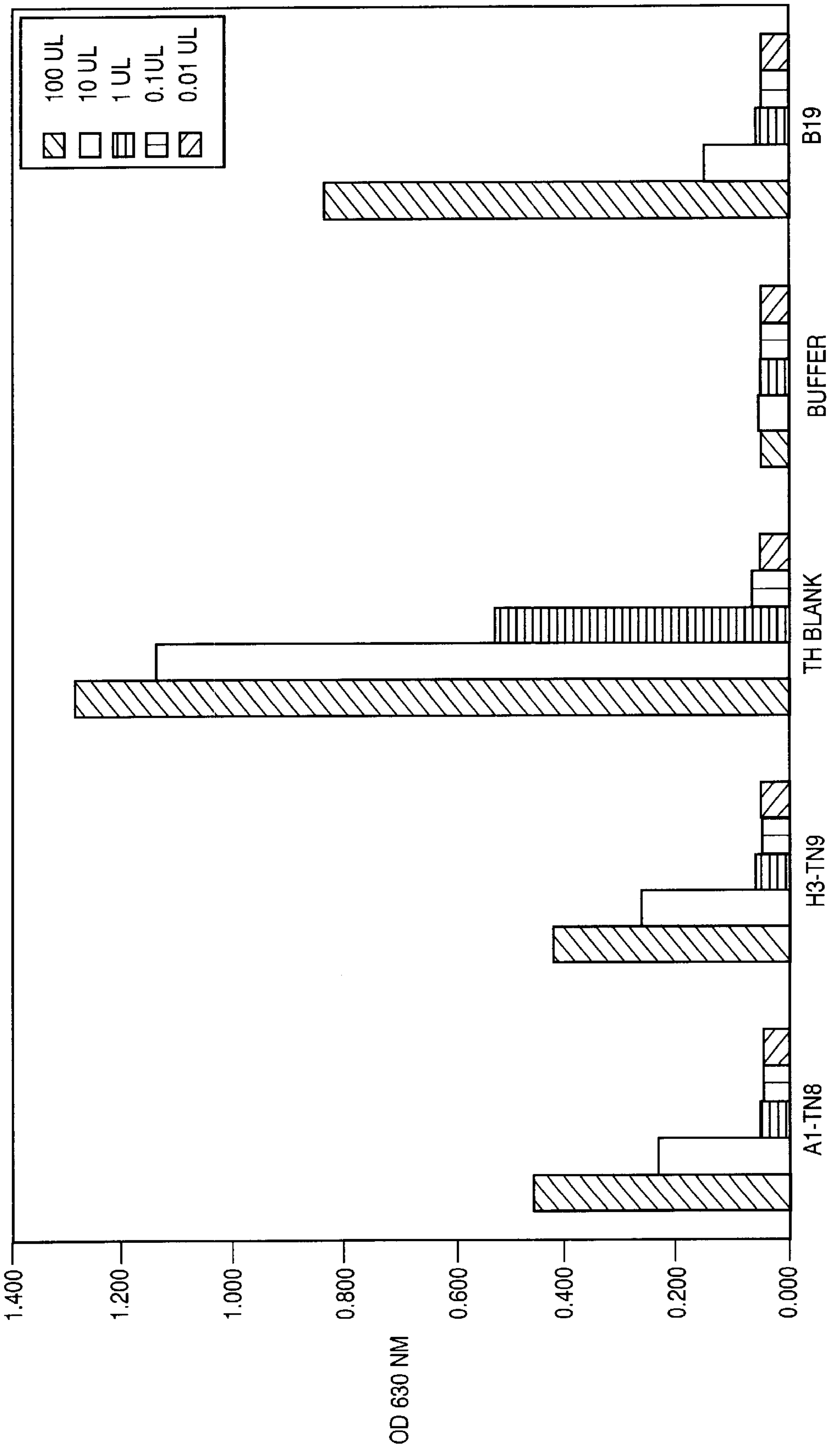
FIG. 1 shows results of an ELISA testing the ability of peptide binding moieties according to the invention, immobilized on beads, to bind to B19 capsid proteins (VP1–VP2).

The present invention makes possible the efficient detection and clearing of parvovirus B19 and/or B19-like polypeptides from a solution that contains the virus or like polypeptide with the use of novel binding moieties that are capable of binding to parvovirus B19 or like polypeptide. The preferred binding moieties of the present invention bind parvovirus B19 and/or B19-like polypeptides with high affinity, comparable or superior to other proteins such as antibodies known to bind parvovirus B19.

Particularly preferred polypeptide binders for B19 and/or B19-like polypeptides have been isolated using phage display technology, and the sequences of such polypeptides are described herein. These binding polypeptides and polypeptides including them may be easily produced in any known way, including chemical synthesis, production in transformed host cells expressing polynucleotides that encode the binding polypeptides (e.g., such as recombinantly transformed bacteria, yeast, fungi, insect cells, and mammalian cells), secretion from genetically engineered organisms (e.g., transgenic mammals) in biological fluids or tissues such as urine, blood, milk, etc.

Isolation of B19 Binding Moieties Using Phage Display

In order to isolate new polypeptide binding moieties for parvovirus B19 and/or B19-like polypeptides (B19 and/or B19 like binding peptides), screening of large peptide libraries, for example using phage display techniques, is especially advantageous, in that very large numbers (e.g., $5\times10^9$) of potential binders can be tested and successful binders isolated in a short period of time. As described in the examples below, polypeptides according to the present invention were isolated using phage display methods to screen filamentous phage libraries.

Where large peptide libraries are screened, it is possible to run the screening process to force the isolation of binding moieties satisfying particular conditions of binding and release. To do this, two solution conditions may be preselected, i.e., binding conditions and release conditions. The binding conditions are a set of solution conditions under which it is desired that a discovered binding moiety will bind the target, in this case parvovirus B19 and/or B19-like polypeptides. The release conditions are a set of solution conditions under which it is desired that a discovered binding moiety will not bind the parvovirus, that is, conditions under which the binding moiety will dissociate from the virus. The two conditions may be selected to satisfy any criterion of the practitioner, such as ease of attaining the conditions, compatibility with other purification steps, lowered cost of switching between conditions compared to other affinity media, etc. For example, if the object is to clear parvovirus B19 from blood, binding conditions would suitably be the conditions of temperature, pH, etc. at which blood is handled or stored; and release conditions would advantageously differ from the binding conditions with respect to at least one parameter. Polypeptides may be isolated according to the present invention which are suitable for such a clearing operation, for example, if they are found to bind parvovirus B19 and/or B19-like polypeptides at physiological pH (i.e., ~pH 7.4) and to maintain binding, e.g., until the pH is substantially lowered (e.g., to about pH 2). Such peptides can be immobilized on a solid substrate and contacted with whole blood, and the viral particles will bind to the peptide-bearing substrate until the blood is removed. The substrate can be recycled by a sanitization procedure that includes a release condition, such as low pH, to clear the substrate of virus, after which procedure the substrate can be reused.

Selection of a Parental Binding Domain (Template)

In order to prepare a library of potential polypeptides to screen for binding moieties such as parvovirus B19 binding peptides, a candidate binding domain is selected to serve as a structural template for the peptides to be displayed in the library. The library is made up of analogues of the parental domain or template. The binding domain template may be a naturally occurring or synthetic protein, or a region or domain of a protein. The binding domain template may be selected based on knowledge of a known interaction between the binding domain template and parvovirus B19 and/or B19-like polypeptides, but this is not critical. In fact, it is not essential that the domain selected to act as a template have any affinity for parvovirus B19 at all: Its purpose is to provide a structure from which a multiplicity (library) of analogues can be generated, which multiplicity of analogues will hopefully include one or more analogues that exhibit the desired binding and release properties (and any other properties screened for). Thus, the binding conditions and the release conditions discussed above may be selected with knowledge of the exact polypeptide that will serve as the parental binding domain, or with knowledge of a class of proteins or domains to which the domain belongs, or completely independently of the choice of the parental binding domain. Similarly, the binding and/or release conditions may be selected with regard to known interactions between a binding domain and parvovirus B19 and/or B19-like polypeptides, e.g., to favor the interaction under one or both of the solution conditions, or they may be selected without regard to such known interactions. Likewise, the binding domain template can be selected taking into account the binding and/or release conditions or not, although it must be recognized that if the binding domain analogues are unstable under the binding or release conditions, useful binding moieties may not be isolated.

The nature of the parental binding domain greatly influences the properties of the derived polypeptides (analogues) that will be tested against parvovirus B19 and/or B19-like polypeptide targets. In selecting the parental binding domain, the most important consideration is how the analogue domains will be presented to the parvovirus, i.e., in what conformation the virus and the analogues will come into contact. In preferred embodiments, for example, the analogues will be generated by insertion of synthetic DNA encoding the analogue into a replicable genetic package, preferably phage, resulting in display of the domain on the surface of a microorganism, such as M13 phage, using techniques as described, e.g., in Kay et al., *Phage Display of Peptides and Proteins: A Laboratory Manual* (Academic Press, Inc., San Diego 1996) and U.S. 5,223,409 (Ladner et al.), incorporated herein by reference.

For formation of phage display libraries, it is preferred to use a structured polypeptide as the binding domain template, as opposed to an unstructured, linear peptide. Mutation of surface residues in a protein will usually have little effect on the overall structure or general properties (such as size, stability, and temperature of denaturation) of the protein; while at the same time mutation of surface residues may profoundly affect the binding properties of the protein. The more tightly a polypeptide segment is constrained, the less likely it is to bind to any particular target; however if the polypeptide does bind, the binding is likely to be of higher affinity and of greater specificity. Thus, it is preferred to select a parental domain and, in turn, a structure for the polypeptide analogues, that is constrained within a framework having some degree of rigidity.

Preferably the protein domain that is used as a template or parental domain for the library of domain analogues will be a small protein or polypeptide. Small proteins or polypeptides offer several advantages over large proteins: First, the mass per binding site is reduced. Highly stable protein domains having low molecular weights, e.g., Kunitz domains (~7 kDa), Kazal domains (~7 kDa), Cucurbida maxima trypsin inhibitor (CMTI) domains (~3.5 kDa), and endothelin (~2 kDa), can show much higher binding per gram than do antibodies (150 kDa) or single-chain antibodies (30 kDa). Second, the possibility of non-specific binding is reduced because there is less surface available. Third, small proteins or polypeptides can be engineered to have unique tethering sites in a way that is impracticable for larger proteins or antibodies. For example, small proteins can be engineered to have lysines only at sites suitable for tethering (e.g., to a chromatography matrix), but this is not feasible for antibodies. Fourth, a constrained polypeptide structure is more likely to retain its functionality when transferred with the structural domain intact from one framework to another. For instance, the binding domain structure is likely to be transferable from the framework used for presentation in a library (e.g., displayed on a phage) to an isolated protein removed from the presentation framework or immobilized on a chromatographic substrate.

Immobilization of the polypeptides according to the invention is contemplated, e.g., onto chromatographic matrices to form efficient B19 binding substrates for use with solutions such as whole blood or culture media. By selecting appropriate binding domain templates, binding polypeptides having a single free (unpaired with another cysteine that ordinarily forms a disulfide link) cysteine can be isolated. Such thiol-functional polypeptides can be used for highly stable immobilization to substrates by formation of a thioether with iodoacetamide, iodoacetic acid, or similar α-iodo carboxylic acid groups.

Similarly, the C-terminal carboxyl group of the peptide domain may be converted to a hydrazide (—NH—$NH_2$), for reaction with an aldehyde-functional or other reactive substrate. This technique is preferred.

There are many small, stable protein domains suitable for use as parental domains and for which the following useful information is available: (1) amino acid sequence, (2) sequences of several homologous domains, (3) 3-dimensional structure, and/or (4) stability data over a range of pH, temperature, salinity, organic solvent, oxidant concentration. Some examples are: Kunitz domains (58 amino acids, 3 disulfide bonds), Cucurbida maxima trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds). Most but not all of these contain disulfide bonds that rigidify and stabilize the structure. The binding domain will preferably be based on a single loop (one disulfide) of a microprotein that is homologous to a known protein domain or not. For example, constrained loops of 7 to 9 amino acids were used as templates to form libraries for isolating parvovirus B19 binding moieties disclosed herein. Libraries based on these domains, preferably displayed on phage, can be readily constructed and used for the selection of binding moieties according to this invention.

Providing a Library of Parental Domain Analogues

Once a template domain has been selected, a library of potential binding moieties is created for screening against the parvovirus B19 or its capsid protein VP1–VP2 at the binding and elution (release) conditions. The library is created by making a series of analogues or mutations, each analogue corresponding to the candidate binding domain except having one or more amino acid substitutions in the sequence of the domain. The amino acid substitutions are expected to alter the binding properties of the domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximize the effect of substitutions. In addition, extra amino acids can be added into the structure of the candidate binding domain.

The object of creating the library of domain analogues is to provide a great number of potential binding moieties for reaction with the B19 and/or B19-like polypeptides, particularly the VP1–VP2 capsid structure. In general, the greater the number of analogues in the library, the greater the likelihood that a member of the library will bind to VP1–VP2. Designed libraries following a particular template structure and limiting amino acid variegation at particular positions are much preferred, since a single library can encompass all the designed analogues and the included sequences will be known and presented in roughly equal numbers. By contrast, random substitution at only six positions in an amino acid sequence provides over 60 million analogues, which is a library size that begins to present practical limitations even when utilizing screening techniques as powerful as phage display. It is therefore preferred to create a designed or biased library, in which the amino acid positions designated for variation are considered so as to maximize the effect of substitution on the binding characteristics of the analogue, and the amino acid residues allowed or planned for use in substitutions are limited, e.g., on the basis that they are likely to cause the analogue to bind under the solution conditions at which the library will be screened for binders.

As indicated previously, the techniques discussed in Kay et al., *Phage Display of Peptides and Proteins: A Laboratory Manual* (Academic Press, Inc., San Diego 1996) and U.S. Pat. No. 5,223,409 are particularly useful in preparing a library of analogues corresponding to a selected parental domain, which analogues will be presented in a form suitable for large-scale screening of large numbers of analogues with respect to a target parvovirus B19 or a B19-like polypeptide, e.g., VP1–VP2. The use of replicable genetic packages, and most preferably phage display, is a powerful method of generating novel polypeptide binding entities that involves introducing a novel DNA segment into the genome of a bacteriophage (or other amplifiable genetic package) so that the polypeptide encoded by the novel DNA appears on the surface of the phage. When the novel DNA contains sequence diversity, then each recipient phage displays one variant of the initial (parental) amino acid sequence encoded by the DNA, and the phage population (library) displays a vast number of different but related amino acid sequences.

A phage library is contacted with and allowed to bind the target, in this case parvovirus B19 and/or B19-like polypeptides, e.g., purified VP1 and VP2 structural proteins, mimicking the outer surface (capsid) of the parvovirus. Non-binders are separated from binders (which are complexed with the target). The bound phage are liberated from the B19 target by disassociation, e.g., at low pH (e.g., pH less than 5, most preferably about pH 2) and then amplified. Since the phage can be amplified through infection of bacterial cells, even a few binding phage are sufficient to reveal the gene sequence that encodes a binding moiety. Using these techniques it is possible to recover a binding phage that is about 1 in 20 million in the library population. One or more libraries, displaying 10–20 million or more potential binding polypeptides each, can be rapidly screened to find high-affinity B19 and/or B19-like polypeptide binding moieties. When the selection process works, the diversity of the population falls with each round until only good binders remain, i.e., the process converges. Typically, a phage display library will contain several closely related binders (10 to 50 binders out of more than 10 million). Indications of convergence include increased binding (measured by phage titers) and recovery of closely related sequences. After a first set of binding polypeptides is identified, the sequence information can be used to design other (secondary) libraries biased for members having additional desired properties.

Such techniques make it possible not only to screen a large number of analogues but make it practical to repeat the binding/elution cycles and to build secondary, biased libraries for screening analog-displaying packages that meet desired criteria. In this manner a phage display library is made to reveal members that bind tightly (i.e., with high affinity) under the screening conditions.

Use of the Binding Moieties in Detection and Removal of B19 and Like Proteins After B19 binding moieties are isolated from one or more libraries that exhibit the desired affinity under binding conditions and the desired dissociation under release conditions, preparation of isolated binding moieties can be accomplished in several known ways. If, for example, the binding moieties are identified from a phage display library (i.e., by isolation of B19 binder phage), released phage can be recovered, propagated, the exogenous (non-native) DNA insert encoding the binders isolated and amplified, the DNA sequence analyzed and any desired quantity of the binder prepared, e.g., by direct synthesis of the polypeptide or recombinant expression of the isolated DNA or an equivalent coding sequence. Direct synthesis of the peptides of the invention may be accomplished using conventional techniques including, preferably, solid-phase peptide synthesis, although solution-phase synthesis may also be used. In solid-phase synthesis, for example, the synthesis is commenced from the carboxy-terminal end of the peptide using an α-amino protected amino acid. t-Butyloxycarbonyl (Boc) protective groups can be used for all amino groups, though other protective groups are suitable. See, Stewart et al., *Solid-Phase Peptide Synthesis* (1989), W. H. Freeman Co., San Francisco; and Merrifield, *J. Am. Chem. Soc.,* 85:2149–2154 (1963).

Polypeptides according to the invention may also be prepared commercially by companies providing peptide synthesis as a service (e.g., BACHEM Bioscience, Inc., King of Prussia, Pa.; Quality Controlled Biochemicals, Inc., Hopkinton, Mass.).

The B19 binding moieties thus isolated will be extremely useful for detection and/or clearing of parvovirus B19 and/or B19-like polypeptides from any solution that contains it. Any suitable method of assaying or purification may be employed.

For detection of parvovirus B19 and/or B19-like polypeptides in a solution such as blood suspected of containing it, a binding moiety can be detectably labeled, e.g., radiolabeled or enzymatically labeled, then contacted with the solution, and thereafter formation of a complex between the binding moiety and the virus can be detected. A phage binding moiety according to the invention, i.e., a recombinant phage displaying a B19 binder polypeptide on its surface, may form a complex with parvovirus B19 that is detectable as a sediment in a reaction tube, which can be detected visually after settling or centrifugation.

Alternatively, a sandwich-type assay may be used, wherein a B19 binding moiety is immobilized on a solid support such as a plastic tube or well, or on a chromatographic matrix such as sepharose beads, then the solution suspected of containing B19 and/or B19 like virus is contacted with the immobilized binding moiety, non-binding materials are washed away, and complexed virus is detected using a suitable detection reagent, such as a monoclonal antibody recognizing B19, which reagent is detectable by some conventional means known in the art, including being detectably labeled, e.g., radiolabeled or labeled enzymatically, as with horseradish peroxidase and the like.

For removal of parvovirus B19 from a solution, a binding moiety of the invention can be immobilized on a solid substrate such as a chromatographic support or other porous material, then the immobilized affinity ligand can be loaded or contacted with the solution under conditions suitable for formation of a binding moiety/parvovirus B19 complex. The non-binding portion of the solution can be removed or collected substantially free from parvovirus B19 and/or B19-like polypeptides.

Alternatively, bulk clearing of infected solutions such as whole blood or blood products can be carried out with one or more binding moieties of the invention by adding the binding moiety to the solution and allowing the binding to the parvovirus B19 and/or B19-like polypeptide to occur, then isolating the complex from the uncontaminated remainder by centrifugation, filtration or any other suitable means of separation. For this alternative method, binding moieties that are in the form of B19-binder-displaying bacteriophage are most advantageous, and are preferred.

Many parvoviruses are known, and human or veterinary vaccines have been studied that have as an active immunogen a fragment of a parvovirus such as a portion of the capsid, or a recombinant preparation of capsid proteins, e.g., expressed in a baculovirus expression system. See, e.g., U.S. Pat. No. 5,498,413 and WO 91/12269. In such situations, purification of B19 proteins (i.e., involving not only separation but recovery of B19-like polypeptides) may be desirable, and the binding moieties according to this invention are especially useful for that purpose. For purification, binding moieties according to the present invention can be immobilized on a chromatographic support, the production stream or recombinant cell culture medium containing the intended parvovirus vaccine product may be contacted with the binding moiety-bearing support under conditions permitting binding, then the bound parvovirus vaccine product can be eluted and collected for further formulation into a useful vaccine against parvovirus.

Isolation of parvovirus B19 binding moieties in accordance with this invention will be further illustrated below. The specific parameters included in the following examples are intended to illustrate the practice of the invention, and they are not presented to in any way limit the scope of the invention.

EXAMPLE I

Screening of Phage Display Libraries

For screening libraries to isolate binding moieties for parvovirus B19, a surrogate target was obtained, consisting of purified, recombinant B19 capsid proteins VP1 and VP2 (VP1–VP2). Suitable preparations of VP1–VP2 can be made according to methods described in U.S. Pat. No. 5,498,413 or WO 91/12269, incorporated herein by reference. Prior to screening against phage display libraries, partially purified VP1–VP2 was immobilized on dextrin-coated microtiter wells (Recti-Bind™; Pierce Chemical Co.) and tested using standard ELISA techniques, to ensure that under the screening conditions there was a low background level of phage recovered.

Three libraries, designated TN7 ($5\times10^9$ amino acid sequence diversity), TN8 ($6\times10^9$ amino acid sequence diversity), and TN9 ($5\times10^9$ amino acid sequence diversity), were constructed for expression of diversified polypeptides on M13 phage. Each library was screened for binders to purified VP1–VP2. Each of the libraries was constructed to display a microprotein based on an 11- or 12-amino acid template. The TN7 library utilized a template sequence of Xaa-Xaa-Cys-Xaa-Xaa-Xaa-Xaa-Xaa-Cys-Xaa-Xaa (SEQ ID NO:24); the TN8 library utilized a template sequence of Xaa-Xaa-Cys-Xaa-Xaa-Xaa-Xaa-Xaa-Xaa-Cys-Xaa-Xaa (SEQ ID NO:25); the TN9 library utilized a template sequence of Xaa-Cys-Xaa-Xaa-Xaa-Xaa-Xaa-Xaa-Xaa-Cys-Xaa (SEQ ID NO:26).

Four or five rounds of screening were performed with each library. Each round consisted of a binding step (incubation for, e.g., 1 hour), a wash procedure to remove unbound phage and non-specifically bound phage, and an elution step to capture VP1–VP2 binder phage (e.g., elution with pH 2 buffer). The recovered phage were propagated and used in the binding step of the succeeding round. After each round, the phage eluted were counted to determine if a convergent screening process was occurring. A convergent screen is one in which the fraction of input increases over successive rounds, indicating that the diversity of the phage library is being reduced. This is a desired result, because it indicates that a ligand candidate for the immobilized target molecule is potentially being selected from the population.

EXAMPLE II

Analysis of Individual Isolates

From convergent screens of phage display libraries, eluted phage were propagated and 376 phage isolates were selected randomly and individually tested for binding to VP1–VP2 by standard ELISA techniques, using a polyclonal anti-phage antibody to detect bound phage. Briefly, VP1–VP2 (2 μl per well) was coated on dextrin plates, blocked with BSA, and individual phage isolates were added to the wells (50 μl, $10^9$ pfu per well). After washing, bound phage were incubated with the detection anti-phage antibodies (100 μl per well HRP-conjugated anti-M13 antibody in PBS-Tween (Pharmacia Inc.)). Wild type phage, displaying no non-phage peptide, were employed as controls. The bound antibody was detected by adding 100 μl per well of two-component TMB (tetramethylbenzidine; Kirkegaard & Perry).

Phage isolates that provided three times signal above background were declared binders. DNA coding for the B19-binding polypeptides was isolated from positive phage, sequenced, and the amino acid sequence deduced.

The amino acid sequence data from these phage isolates were grouped by library and sorted according to the degree of similarity. In all of the sequenced isolates, some homology amongst the selectants was seen: Of the 32 isolates sequenced from the TN7 library, 17 had the same sequence; 29 out of 36 from the TN8 isolates had an identical sequence and two sequences predominated the TN9 isolates (9 and 10 out of 23). Of greatest interest were those isolates that gave a strong ELISA signal, as they were the strongest binders of VP1–VP2. Preferred parvovirus B19 binding polypeptides were identified by having (1) significantly higher binding affinity for the target VP1–VP2 than the control phage, (2) a significantly higher binding affinity for the target under binding conditions, and (3) little or no binding to BSA. These polypeptides are set forth in Tables 1–3 below:

TABLE 1

Amino acid sequences of B19-binding polypeptides from the TN7 library

| TN7 isolate | sequence | frequency | ELISA signal | relative binding | SEQ ID NO: |
|---|---|---|---|---|---|
| A07 | F F C G F W H D C H P | 2/32 | 0.7 | 27 | 4 |
| A12 | F S C L W F P F C P D | 17/32 | 0.5 | 28 | 5 |
| B11 | F F C A L W P S C H H | 2/32 | 0.5 | 31 | 6 |
| B12 | L F C H F W Y N C D F | 2/32 | 0.7 | 29 | 7 |
| D11 | L F C S F W Y N C D A | 1/32 | 0.9 | 35 | 8 |
| F12 | L F C S F W Y N C D D | 1/32 | 0.9 | — | 9 |
| H09 | L F C R F W Y N C S A | 2/32 | 0.6 | — | 10 |
| C11 | F F C Q Y W Y N C D - | 1/32 | 0.7 | 26 | 11 |
| E11 | - F C R F W Y G C H P | 3/32 | 0.6 | 33 | 12 |

TABLE 2

Amino acid sequences of B19-binding polypeptides from the TN8 library

| TN8 isolate | sequence | frequency | ELISA signal | relative binding | SEQ ID NO: |
|---|---|---|---|---|---|
| A01 | F F C S F W H G G C D D | 29/36 | 1.6 | 52 | 13 |
| A05 | A F C H F W F H G C D D | 5/36 | 1.3 | 30 | 14 |
| C01 | A F C W L W P G N C L H | 1/36 | 1.5 | 44 | 15 |
| D06 | H F C H F W F G G C P H | 1/36 | 1.3 | 40 | 16 |

TABLE 3

Amino acid sequences of B19-binding polypeptides from the TN9 library

| TN9 isolate | sequence | frequency | ELISA signal | relative binding | SEQ ID NO: |
|---|---|---|---|---|---|
| D01 | F C W L W P S S D C F | 9/23 | 0.7 | 36 | 17 |
| H03 | F C W L W P A H S C H | 10/23 | 0.8 | 85 | 18 |
| E03 | F C H L W W P F Q C A | 2/23 | 0.8 | 40 | 19 |
| A06 | F C Q L W W P F Q G A | 1/23 | 0.7 | — | 20 |
| F01 | L C P A H W Q F W C D | 1/23 | 0.5 | — | 21 |

Based on the ELISA data and the sequence similarities within each library, the 18 isolates (Tables 1–3) were selected and evaluated further with respect to their binding characteristics to VP1–VP2. Relative binding of each isolate was studied by ELISA. Each selected phage isolate, held at a constant amount, was contacted with decreasing amounts per well of VP1–VP2, the amounts coating each dextrin well varying from 2 μl down to 0.001 μl. Bound phage were detected as described before using polyclonal anti-phage antibody. All of the phage isolates displayed a dose response curve to the varying concentrations of VP1–VP2. Normalizing this binding data as a percent of the OD 630 nm values observed for each isolate indicated that each isolate had its own binding characteristics, with H03-TN9 being the strongest binder. Using VP1–VP2 at 1:10 dilution as an arbitrary point, a value for the signal was interpolated, and the relative binding strengths are reflected in Tables 1–3, above.

Based on these values, A01-TN8 and H03-TN9, as the two highest-ranking isolates, were selected for further study.

EXAMPLE III

Further Characterization of TN8 and TN9 Isolates

The AO1-TN8 and H03-TN9 polypeptides were synthesized by Bachem Bioscience (King of Prussia, Pa.) using solid-phase synthesis. The synthesized peptides were modified to incorporate a spacer sequence (Glu-Gly-Gly-Gly-Ser; SEQ ID NO:27) and a hydrazide functionality (—NH—NH2) at the carboxy terminus. The hydrazide function permits labeling or immobilization on aldehyde-functional media, and the spacer sequence, based on a naturally occurring spacer sequence in M13 bacteriophage gene III, permits the polypeptides to extend away from a support to which it is bound.

After synthesis and cleavage from the solid support, the peptides were cyclized by establishing a disulfide bond between the two cysteines, purified by reverse HPLC and analyzed by mass spectrometry, amino acid analysis, reverse-phase HPLC to confirm purity. The sequence of A01-TN8 including the spacer sequence was determined to be Ala-Glu-Gly-Thr-Gly-Asp-Phe-Phe-Cys-Ser-Phe-Trp-His-Gly-Gly-Cys-Asp-Asp-Asp-Pro-Gly-Pro-Glu-Gly-Gly-Gly-Ser (SEQ ID NO:22) and the sequence of H03-TN9 including the spacer sequence was Ala-Glu-Gly-Thr-Gly-Asp-Phe-Cys-Trp-Leu-Trp-Pro-Ala-His-Ser-Cys-His-Asp-Pro-Gly-Pro-Glu-Gly-Gly-Gly-Ser (SEQ ID NO:23).

The two peptide ligands were immobilized on an aldehyde-functional methacrylate resin support (TosoHaas formyl 750-M; Montgomeryville, Pa.). The peptides were first weighed and dissolved into immobilization buffer (100 mM NaOAc, 150 mM NaCi, 0.1% Tween 20, pH 5.0). A sample of the dissolved peptides was taken for concentration analysis. The chromatography media was measured and washed twice with immobilization buffer. The media and peptide were mixed together and tumbled overnight at room temperature. After the reaction, the supernatant was analyzed for residual peptide and the resultant B19 affinity media was washed with deionized water, 1M NaCl, Tris buffer with 1M NaCl, and twice with PBS. The immobilization data are set forth below:

| polypeptide | amount added (mg) | starting peptide (mg) | peptide on media (mg) | volume of media (mL) | ligand density (mg/mL) | ligand density (μmol/mL) |
|---|---|---|---|---|---|---|
| A01-TN8 | 3.2 | 2.56 | 1.59 | 1.5 | 1.1 | 0.41 |
| H03-TN9 | 3.3 | 2.64 | 2.11 | 1.5 | 1.4 | 0.53 |

These parvovirus B19 affinity media were evaluated for the ability of the immobilization ligand to recognize and bind to parvovirus B19 capsid proteins VP1–VP2. Each of the prepared media was evaluated for its ability to deplete a solution of parvovirus B19 capsid proteins as compared to a blank control (media only). 100 μl of each media were aliquoted and washed three times with 1 ml of stabilizing buffer (0.5% gelatin, 2% BSA, 1.5% Tween 20 in PBS). The capsid protein stock solution was prepared by diluting 30 μl of the purified capsid protein solution (Absorbance at 280 nm=2) with 320 μl of stabilizing buffer. 300 μl of stabilizing buffer and 100 μl of capsid stock solution were added to 100 μl of each media. The mixtures were gently tumbled for 1 hour at room temperature. After incubation, the mixtures were centrifuged at 6000 rpm for 1 minute, and the supernatants were sampled for analysis.

Each sample was analyzed with a standard ELISA for the presence or absence of B19 capsid proteins at ten-fold serial dilution into stabilizing buffer. Detection was with the use of a monoclonal anti-parvovirus B19 antibody (Chemicon MAb 8292). A negative control for the assay was stabilizing buffer alone, and a positive control was a 1:50 dilution of the initial capsid stock solution. FIG. 1 summarizes the ELISA signals at a 5-minute incubation time point in the assay. In the figure, the dilutions are designated as follows: 100 μl sample=neat supernatant; 10 μl=1:10 dilution, 1 μl=1:100 dilution, 0.1 μl=1:1,000 dilution, 0.01 μl=1:10,000 dilution. The data clearly show that both ligands deplete the solution of capsid proteins significantly more than the control blank beads.

The analysis above demonstrates that immobilized forms of both A01-TN8 and H03-TN09 are able to effectively bind parvovirus B19 capsid proteins and clear them from solution. The ELISA signals of the neat and 1:10 supernatant from the affinity media are less than the signals of 1:10 and 1:100 supernatants from the TH blank media, respectively. Also, the affinity media supernatant signals are similar to the 1:50 dilution of the capsid stock solution. The results illustrate that these affinity media according to the invention are effectively removing B19 capsid protein from the solution in a batch binding study.

Following the foregoing description, the characteristics important for the detection of parvovirus in a solution or separation of parvovirus B19 and/or B19-like polypeptides from any solution can be appreciated. Additional embodiments of the invention and alternative methods adapted to a particular solution to be cleared of or analyzed for B19 or B19-like polypeptides will be evident from studying the foregoing description. All such embodiments and obvious alternatives are intended to be within the scope of this invention, as defined by the claims that follow.

Each of the publications referred to above is hereby incorporated by reference.

---

What is claimed is:

1. An isolated binding moiety for human parvovirus B19 or a fragment thereof that is immunological cross-reactive with human parvovirus B19, which binding moiety is a polypeptide comprising an amino acid sequence of the formula:

I. Xaa-Xaa-Cys-Xaa-Xaa-Xaa-Xaa-Xaa-Cys-Xaa-Xaa (SEQ ID NO:24); or

II. Xaa-Xaa-Cys-Xaa-Xaa-Xaa-Xaa-Xaa-Xaa-Cys-Xaa-Xaa (SEQ ID NO:25); or

-continued

III. Xaa-Cys-Xaa-Xaa-Xaa-Xaa-Xaa-Xaa-Xaa-Cys-Xaa (SEQ ID NO:26); where

Xaa can be any amino acid, with the proviso that said polypeptide is capable of binding to said virus or fragment thereof in a solution at physiological pH and dissociating from said virus in a solution at pH 2.

* * * * *